(12) United States Patent
McAlister

(10) Patent No.: US 9,206,045 B2
(45) Date of Patent: Dec. 8, 2015

(54) REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS

(75) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

(21) Appl. No.: 13/026,996

(22) Filed: Feb. 14, 2011

(65) Prior Publication Data

US 2011/0200516 A1    Aug. 18, 2011

Related U.S. Application Data

(60) Provisional application No. 61/304,403, filed on Feb. 13, 2010.

(51) Int. Cl.
*C01B 3/24* (2006.01)
*B01J 19/12* (2006.01)
(Continued)

(52) U.S. Cl.
CPC ............. *C01B 3/24* (2013.01); *B01J 19/127* (2013.01); *B01J 19/1812* (2013.01); *B01J 19/20* (2013.01); *F24J 2/07* (2013.01); *G01N 35/00871* (2013.01); *B01J 2219/00085* (2013.01);
(Continued)

(58) Field of Classification Search
CPC ...... B01J 19/127; B01J 19/20; B01J 19/1812; B01J 2219/00085; B01J 2219/187; B01J 19/088; B01J 2219/0894; C01B 3/24; C01B 2203/0266; C01B 2203/04; C01B 2203/0465; C01B 2203/0485; C01B 2203/0811; C01B 2203/0822; C01B 2203/0872; G01N 35/00871; G01N 1/405; G01N 35/00613; G01N 2201/021; F24J 2/07; Y02E 60/364; Y02E 10/41
See application file for complete search history.

(56) References Cited

U.S. PATENT DOCUMENTS 3,613,792 A   10/1971   Hyde et al.
3,633,372 A    1/1972   Kimmel et al.
(Continued)

FOREIGN PATENT DOCUMENTS

CA   2521698 A1   8/2005
CN   101042261 A   9/2007
(Continued)

OTHER PUBLICATIONS

Elais et al "Control of Grapheen's Properties by Reversible Hydrogenation: Evidence of Graphene", Science, vol. 323, No. 5914, p. 610-613.*

(Continued)

*Primary Examiner* — Xiuyu Tai
(74) *Attorney, Agent, or Firm* — Perkins Coie LLP

(57) ABSTRACT

Reactor vessels with transmissive surfaces for producing hydrogen-based fuels and structural elements, and associated systems and methods. A chemical reactor in accordance with a particular embodiment includes a reactor vessel having a reaction zone, a hydrogen donor source coupled in fluid communication with the reaction zone, and a steam source coupled in fluid communication with the reaction zone. The reactor further includes a transmissive surface at the reaction zone, with the transmissive surface being transmissive to a reactant entering the reaction zone and/or radiant energy entering the reaction zone.

23 Claims, 7 Drawing Sheets

(51) Int. Cl.
*B01J 19/18* (2006.01)
*B01J 19/20* (2006.01)
*F24J 2/07* (2006.01)
*G01N 1/40* (2006.01)
*G01N 35/00* (2006.01)
*G01N 1/02* (2006.01)

(52) U.S. Cl.
CPC ... *B01J 2219/187* (2013.01); *C01B 2203/0266* (2013.01); *C01B 2203/04* (2013.01); *C01B 2203/0465* (2013.01); *C01B 2203/0485* (2013.01); *C01B 2203/0811* (2013.01); *C01B 2203/0822* (2013.01); *C01B 2203/0872* (2013.01); *C01B 2203/0883* (2013.01); *G01N 1/405* (2013.01); *G01N 35/00613* (2013.01); *G01N 2001/021* (2013.01); *Y02E 10/41* (2013.01); *Y02E 60/364* (2013.01)

(56) References Cited

U.S. PATENT DOCUMENTS

| | | |
|---|---|---|
| 3,662,832 A | 5/1972 | Keeler et al. |
| 3,757,860 A | 9/1973 | Pritchett |
| 3,788,389 A | 1/1974 | Waters |
| 3,807,491 A | 4/1974 | Van Hulsen |
| 3,830,508 A | 8/1974 | Endicott |
| 3,840,068 A | 10/1974 | Waters |
| 3,882,937 A | 5/1975 | Robinson |
| 3,936,652 A | 2/1976 | Levine |
| 3,975,912 A | 8/1976 | Greene |
| 3,986,362 A | 10/1976 | Baciu |
| 3,990,502 A | 11/1976 | Best |
| 3,991,817 A | 11/1976 | Clay |
| 4,019,868 A | 4/1977 | Sebacher et al. |
| 4,053,576 A | 10/1977 | Fletcher |
| 4,070,861 A | 1/1978 | Scragg et al. |
| 4,082,865 A | 4/1978 | Ban et al. |
| 4,099,489 A | 7/1978 | Bradley |
| 4,138,993 A | 2/1979 | Conley |
| 4,158,354 A | 6/1979 | Carden |
| 4,161,211 A | 7/1979 | Duffy et al. |
| 4,169,460 A | 10/1979 | Popovich et al. |
| 4,172,506 A | 10/1979 | Terry |
| 4,178,987 A | 12/1979 | Bowman et al. |
| 4,229,184 A | 10/1980 | Gregg |
| 4,257,239 A | 3/1981 | Partin |
| 4,343,338 A | 8/1982 | Hart |
| 4,382,189 A | 5/1983 | Wilson |
| 4,386,801 A | 6/1983 | Chapman et al. |
| 4,401,689 A | 8/1983 | Ban |
| 4,455,045 A | 6/1984 | Wheeler |
| 4,519,342 A | 5/1985 | Yoon |
| 4,549,078 A | 10/1985 | Monahan |
| 4,549,528 A | 10/1985 | Gibson |
| 4,601,508 A | 7/1986 | Kerian |
| 4,611,847 A | 9/1986 | Sullivan |
| 4,620,580 A | 11/1986 | Groezinger et al. |
| 4,704,267 A | 11/1987 | DiMartino |
| 4,706,651 A | 11/1987 | Yudow |
| 4,746,160 A | 5/1988 | Wiesemeyer |
| 4,848,445 A * | 7/1989 | Harper ............... 165/46 |
| 4,921,580 A | 5/1990 | Martes et al. |
| 4,978,162 A | 12/1990 | Labbe |
| 5,058,945 A | 10/1991 | Elliott, Sr. et al. |
| 5,119,897 A | 6/1992 | Moriwake |
| 5,132,090 A | 7/1992 | Volland |
| 5,222,698 A | 6/1993 | Nelson et al. |
| 5,280,990 A | 1/1994 | Rinard |
| 5,315,868 A | 5/1994 | Jacobi et al. |
| 5,348,774 A | 9/1994 | Golecki et al. |
| 5,407,245 A | 4/1995 | Geropp |
| 5,442,934 A | 8/1995 | Wolflick |
| 5,498,059 A | 3/1996 | Switlik |
| 5,560,443 A | 10/1996 | DuBose |
| 5,618,134 A | 4/1997 | Balch |
| 5,647,877 A | 7/1997 | Epstein |
| 5,881,559 A | 3/1999 | Kawamura |
| 5,882,382 A | 3/1999 | Hachisuka et al. |
| 5,986,429 A | 11/1999 | Mula, Jr. |
| 6,012,065 A | 1/2000 | Boucher et al. |
| 6,068,328 A | 5/2000 | Gazdzinski |
| 6,074,696 A | 6/2000 | Sato |
| 6,081,183 A | 6/2000 | Mading et al. |
| 6,089,224 A | 7/2000 | Poulek |
| 6,092,861 A | 7/2000 | Whelan |
| 6,155,212 A | 12/2000 | McAlister |
| 6,200,069 B1 | 3/2001 | Miller |
| 6,216,599 B1 | 4/2001 | Cavanagh |
| 6,220,193 B1 | 4/2001 | Dilks |
| 6,242,752 B1 | 6/2001 | Soma et al. |
| 6,309,010 B1 | 10/2001 | Whitten |
| 6,334,928 B1 | 1/2002 | Sekine et al. |
| 6,378,932 B1 | 4/2002 | Fasel et al. |
| 6,409,252 B1 | 6/2002 | Andrus |
| 6,464,755 B2 | 10/2002 | Nakanishi et al. |
| 6,502,533 B1 | 1/2003 | Meacham |
| 6,508,209 B1 * | 1/2003 | Collier, Jr. ............... 123/3 |
| 6,534,210 B2 | 3/2003 | Luken et al. |
| 6,571,747 B1 | 6/2003 | Gerstweiler |
| 6,585,785 B1 | 7/2003 | Warren et al. |
| 6,630,267 B2 | 10/2003 | Badding et al. |
| 6,749,043 B2 | 6/2004 | Brown et al. |
| 6,756,140 B1 | 6/2004 | McAlister |
| 6,756,565 B2 | 6/2004 | Suenaga et al. |
| 6,838,782 B2 | 1/2005 | Vu |
| 6,854,788 B1 | 2/2005 | Graham |
| 6,897,575 B1 | 5/2005 | Yu |
| 6,919,062 B1 | 7/2005 | Vasileiadis et al. |
| 6,923,004 B2 | 8/2005 | Chandran et al. |
| 6,926,345 B2 | 8/2005 | Ortega et al. |
| 6,979,049 B2 | 12/2005 | Ortega et al. |
| 6,984,305 B2 | 1/2006 | McAlister |
| 7,033,570 B2 | 4/2006 | Weimer et al. |
| 7,140,181 B1 | 11/2006 | Jensen et al. |
| 7,152,908 B2 | 12/2006 | Shahbazi |
| 7,165,804 B2 | 1/2007 | Shahbazi |
| 7,179,383 B1 | 2/2007 | Porter et al. |
| 7,185,944 B2 | 3/2007 | Shahbazi |
| 7,207,620 B2 | 4/2007 | Cosgrove et al. |
| 7,210,467 B2 | 5/2007 | Kweon et al. |
| 7,211,905 B1 | 5/2007 | McDavid, Jr. |
| 7,237,827 B2 | 7/2007 | Shahbazi |
| 7,243,980 B2 | 7/2007 | Vala |
| 7,285,350 B2 | 10/2007 | Keefer et al. |
| 7,293,533 B2 | 11/2007 | Hemsath |
| 7,337,612 B2 | 3/2008 | Skinnes et al. |
| 7,343,971 B2 | 3/2008 | Pfefferle |
| 7,397,141 B2 | 7/2008 | Gouker |
| 7,420,004 B2 | 9/2008 | Hardy et al. |
| 7,426,959 B2 | 9/2008 | Wang et al. |
| 7,449,158 B2 | 11/2008 | Haueter et al. |
| 7,504,739 B2 | 3/2009 | Enis et al. |
| 7,527,094 B2 | 5/2009 | McKinzie et al. |
| 7,568,479 B2 | 8/2009 | Rabinowitz |
| 7,582,167 B2 | 9/2009 | Kaszuba et al. |
| 7,585,339 B2 | 9/2009 | Dahl et al. |
| 7,587,998 B2 | 9/2009 | Hotta et al. |
| 7,597,068 B2 | 10/2009 | Arai et al. |
| 7,608,120 B2 | 10/2009 | Wunning |
| 7,621,262 B2 | 11/2009 | Zubeck |
| 7,628,137 B1 | 12/2009 | McAlister |
| 7,713,642 B2 | 5/2010 | Warner et al. |
| 7,753,122 B2 | 7/2010 | Curlett |
| 7,788,924 B2 | 9/2010 | Hines |
| 7,789,182 B2 | 9/2010 | Bradley et al. |
| 7,799,315 B2 | 9/2010 | Amendola |
| 7,808,121 B1 | 10/2010 | Glynn |
| 7,856,843 B2 | 12/2010 | Enis et al. |
| 7,884,308 B1 | 2/2011 | Mejia |
| 7,955,478 B2 | 6/2011 | McClure |
| 7,963,328 B2 | 6/2011 | Khinkis et al. |
| 7,971,861 B2 | 7/2011 | Soininen |
| 7,972,471 B2 | 7/2011 | Sant |

(56) References Cited

U.S. PATENT DOCUMENTS

| | | |
|---|---|---|
| 8,043,592 B2 | 10/2011 | Krass |
| 8,053,916 B2 | 11/2011 | Edwards et al. |
| 8,187,549 B2 | 5/2012 | McAlister |
| 8,187,550 B2 | 5/2012 | McAlister |
| 8,220,539 B2 | 7/2012 | Vinegar et al. |
| 8,318,100 B2 | 11/2012 | McAlister |
| 8,318,131 B2 | 11/2012 | McAlister |
| 8,318,269 B2 | 11/2012 | McAlister |
| 8,449,634 B2 | 5/2013 | Tamura et al. |
| 2001/0000889 A1 | 5/2001 | Yadav et al. |
| 2002/0102188 A1* | 8/2002 | Hsu et al. ............ 422/168 |
| 2003/0008183 A1 | 1/2003 | Hsu |
| 2003/0019104 A1 | 1/2003 | Smalc |
| 2003/0042128 A1 | 3/2003 | Harutyunyan et al. |
| 2003/0178195 A1 | 9/2003 | Agee et al. |
| 2003/0182861 A1 | 10/2003 | Weimer et al. |
| 2003/0183372 A1 | 10/2003 | Lai et al. |
| 2003/0190569 A1 | 10/2003 | Dafft et al. |
| 2003/0224231 A1 | 12/2003 | Penev |
| 2004/0033455 A1* | 2/2004 | Tonkovich et al. ........ 431/7 |
| 2004/0200618 A1 | 10/2004 | Piekenbrock |
| 2004/0219737 A1 | 11/2004 | Quon |
| 2004/0247957 A1 | 12/2004 | Hatano et al. |
| 2004/0253168 A1 | 12/2004 | Chu |
| 2004/0265448 A1 | 12/2004 | Shiau et al. |
| 2004/0266615 A1 | 12/2004 | Watson et al. |
| 2005/0019234 A1 | 1/2005 | Luo |
| 2005/0029120 A1 | 2/2005 | Bar-Gadda |
| 2005/0061486 A1 | 3/2005 | Yang |
| 2005/0079977 A1 | 4/2005 | Choi et al. |
| 2005/0230085 A1 | 10/2005 | Valenzuela |
| 2005/0265919 A1* | 12/2005 | Lomax et al. ............ 423/651 |
| 2005/0272856 A1 | 12/2005 | Cooper et al. |
| 2006/0005738 A1 | 1/2006 | Kumar |
| 2006/0005739 A1 | 1/2006 | Kumar |
| 2006/0048808 A1 | 3/2006 | Ruckman et al. |
| 2006/0266043 A1 | 11/2006 | Jerome |
| 2007/0028860 A1 | 2/2007 | Hemsath |
| 2007/0031718 A1 | 2/2007 | Fujimura et al. |
| 2007/0065686 A1 | 3/2007 | Fan et al. |
| 2007/0099039 A1* | 5/2007 | Galloway ............ 429/19 |
| 2007/0138006 A1 | 6/2007 | Oakes et al. |
| 2007/0191664 A1 | 8/2007 | Hershkowitz et al. |
| 2007/0194016 A1 | 8/2007 | Dalton |
| 2007/0197376 A1* | 8/2007 | Potapova et al. ........ 502/263 |
| 2007/0205298 A1 | 9/2007 | Harrison et al. |
| 2007/0214986 A1 | 9/2007 | Gaus et al. |
| 2007/0220810 A1 | 9/2007 | Leveson et al. |
| 2008/0086946 A1 | 4/2008 | Weimer et al. |
| 2008/0098654 A1 | 5/2008 | Cherry et al. |
| 2008/0170975 A1* | 7/2008 | Ahn et al. ............ 422/198 |
| 2008/0175766 A1 | 7/2008 | Mankins et al. |
| 2008/0241033 A1 | 10/2008 | Nazri |
| 2008/0295883 A1 | 12/2008 | Ducellier et al. |
| 2008/0314411 A1 | 12/2008 | Mueller et al. |
| 2009/0062591 A1* | 3/2009 | Bingue et al. ............ 585/899 |
| 2009/0071166 A1 | 3/2009 | Hagen et al. |
| 2009/0206666 A1 | 8/2009 | Sella et al. |
| 2009/0232716 A1 | 9/2009 | Rohrich et al. |
| 2009/0258278 A1 | 10/2009 | Steinberg |
| 2009/0313886 A1 | 12/2009 | Hinman et al. |
| 2010/0000874 A1 | 1/2010 | Hinman et al. |
| 2010/0043404 A1 | 2/2010 | Hebbale et al. |
| 2010/0075835 A1* | 3/2010 | Yuge et al. ............ 502/150 |
| 2010/0085713 A1* | 4/2010 | Balandin et al. ............ 361/705 |
| 2010/0107994 A1 | 5/2010 | Moriarty et al. |
| 2010/0140950 A1 | 6/2010 | Pitre |
| 2010/0174124 A1 | 7/2010 | Tonkovich et al. |
| 2010/0242352 A1 | 9/2010 | Perkins et al. |
| 2011/0061295 A1 | 3/2011 | McAlister |
| 2011/0061383 A1 | 3/2011 | McAlister |
| 2011/0100731 A1 | 5/2011 | Hassan |
| 2011/0197599 A1 | 8/2011 | Stewart et al. |
| 2011/0198211 A1 | 8/2011 | McAlister |
| 2011/0200516 A1 | 8/2011 | McAlister |
| 2011/0203776 A1 | 8/2011 | McAlister |
| 2011/0206565 A1 | 8/2011 | McAlister |
| 2011/0207008 A1 | 8/2011 | McAlister |
| 2011/0209979 A1 | 9/2011 | McAlister |
| 2011/0214986 A1 | 9/2011 | Brown |
| 2011/0220040 A1 | 9/2011 | McAlister |
| 2011/0226988 A1 | 9/2011 | McAlister |
| 2011/0230573 A1 | 9/2011 | McAlister |
| 2011/0284298 A1 | 11/2011 | Ajisaka |
| 2011/0315539 A1 | 12/2011 | Zadik et al. |
| 2012/0118878 A1 | 5/2012 | Kim et al. |
| 2012/0119510 A1 | 5/2012 | Herzen et al. |
| 2013/0094909 A1 | 4/2013 | McAlister |
| 2013/0098035 A1 | 4/2013 | McAlister |
| 2013/0101492 A1 | 4/2013 | McAlister |
| 2013/0101502 A1 | 4/2013 | McAlister |
| 2013/0101908 A1 | 4/2013 | McAlister |
| 2013/0136658 A1 | 5/2013 | McAlister |
| 2013/0145761 A1 | 6/2013 | McAlister |
| 2013/0149208 A1 | 6/2013 | McAlister |
| 2013/0149621 A1 | 6/2013 | McAlister |
| 2013/0153399 A1 | 6/2013 | McAlister |
| 2013/0156504 A1 | 6/2013 | McAlister |
| 2013/0158828 A1 | 6/2013 | McAlister |
| 2013/0174486 A1 | 7/2013 | McAlister |
| 2013/0213256 A1 | 8/2013 | McAlister |

FOREIGN PATENT DOCUMENTS

| | | |
|---|---|---|
| CN | 101091900 A | 12/2007 |
| CN | 101597025 A | 12/2009 |
| EA | 200702287 A1 | 4/2008 |
| EP | 1394103 A1 | 3/2004 |
| EP | 1658892 | 5/2006 |
| GB | 24256 | 0/1911 |
| JP | 57136097 A | 8/1982 |
| JP | 59046375 | 3/1984 |
| JP | S62203328 A | 9/1987 |
| JP | 6415132 | 1/1989 |
| JP | 05096149 A | 4/1993 |
| JP | H0637348 | 5/1994 |
| JP | 0725637 | 3/1995 |
| JP | 0940491 | 2/1997 |
| JP | 09055374 | 2/1997 |
| JP | 10172960 | 6/1998 |
| JP | H11108465 A | 4/1999 |
| JP | 2000271472 A | 10/2000 |
| JP | 2000353690 A | 12/2000 |
| JP | 2001080902 A | 3/2001 |
| JP | 2001181846 A | 7/2001 |
| JP | 2001262353 A | 9/2001 |
| JP | 03215670 B2 | 10/2001 |
| JP | 2002158175 A | 5/2002 |
| JP | 2003031506 A | 1/2003 |
| JP | 2003040601 A | 2/2003 |
| JP | 2003166059 A | 6/2003 |
| JP | 2005511467 A | 6/2003 |
| JP | 2003229161 A | 8/2003 |
| JP | 2005021876 A | 1/2005 |
| JP | 2005213069 A | 8/2005 |
| JP | 2007139399 A | 6/2007 |
| JP | 2007150012 A | 6/2007 |
| JP | 2007208076 A | 8/2007 |
| JP | 2007527348 A | 9/2007 |
| JP | 2007254180 A | 10/2007 |
| JP | 2008503709 A | 2/2008 |
| JP | 2008215322 A | 9/2008 |
| JP | 2008310995 A | 12/2008 |
| JP | 2009010263 A | 1/2009 |
| JP | 2009500274 A | 1/2009 |
| JP | 2009513466 A | 4/2009 |
| JP | 2009121412 A | 6/2009 |
| JP | 2009129701 A | 6/2009 |
| JP | 2009274881 A | 11/2009 |
| JP | 2010003568 A | 1/2010 |
| JP | 2010006653 A | 1/2010 |
| JP | 2010-025031 | 2/2010 |
| JP | 2011507218 A | 3/2011 |
| KR | 100794943 | 1/2008 |

(56) References Cited

FOREIGN PATENT DOCUMENTS

| KR | 20120077307 A | 7/2012 |
|---|---|---|
| RU | 1776298 | 11/1992 |
| RU | 2011864 C1 | 4/1994 |
| RU | 2120913 C1 | 10/1998 |
| RU | 2312059 C1 | 12/2007 |
| RU | 2403379 C1 | 11/2010 |
| SU | 1498908 A1 | 8/1989 |
| WO | 9739490 A2 | 10/1997 |
| WO | WO-2007053370 A2 | 5/2007 |
| WO | WO-2007140441 A2 | 12/2007 |
| WO | WO-2008031488 A1 | 3/2008 |
| WO | WO-2008035776 A1 | 3/2008 |
| WO | WO-2008076840 A2 | 6/2008 |
| WO | WO2008/093661 * | 8/2008 |
| WO | WO-2009098375 A1 | 8/2009 |
| WO | WO-2010097890 A1 | 9/2010 |
| WO | WO-2011154945 A2 | 12/2011 |

OTHER PUBLICATIONS

First Action Interview Pilot Program Office Action for U.S. Appl. No. 13/027,015; Applicant: McAlister Technologies, LLC; Date of Mailing: Jul. 29, 2011, 4 pages.

"Zinc Zinc-oxide Thermochemical Cycle." Digital image. Wikipedia, the Free Encyclopedia, Published: Dec. 21, 2008. Accessed: Jan. 4, 2011. Printed: May 20, 2011. <http://en.wikipedia.org/wiki/File:Zinc_zinc-oxide_thermochemical_cycle.jpg>. p. 1.

Chen et al. "Parylene-Encapsulated Copolymeric Membranes as Localized and Sustained Drug Delivery Platforms." Annals of Biomedical Engineering, vol. 37, Issue 10 (Oct. 2009): pp. 2003-2017.

Chen et al. "Thermochemistry Concept Map." Teacherknowledge Wikispace, Published: Nov. 20, 2006. <http://teacherknowledge.wikispaces.com/file/view/Thermochemistry+concept+map+−+Extended.pdf>. p. 1.

Food and Agriculture Organization of the United Nations. "Carbon Sequestration Options under the Clean Development Mechanism to Address Land Degradation." World Soil Resources Reports. Rome, 2000. pp. 1-45.

Foust et al. "An Economic and Evironmental Comparison of a Biochemical and a Thermochemical Lignocellulosic Ethanol Conversion Processes." Cellulose, vol. 16, Issue 4. Jun. 10, 2009. pp. 547-565.

Funk, James E. "Thermochemical Processes for the Production of Hydrogen from Water." College of Engineering, University of Kentucky, Lexington, Kentucky. 1975. pp. 1-9.

Hackett et al. "Evaluation of Conversion Technoloigy Processes and Products: Appendix A—Discussion of Thermochemical Process Definitions." University of California, Davis. Sep. 2004. pp. 1-7.

Kasting, James F. "The Carbon Cycle, Climate, And The Long-Term Effects Of Fossil Fuel Burning." U.S. Global Change Research Information Office. 1998. Web. Accessed: Jul. 1, 2010. Printed: Jun. 13, 2011. <http://www.gcrio.org/CONSEQUENCES/vol4no1/carbcycle.html>.

US Environmental Protection Agency. "EPA Preliminary Analysis of the Waxman-Markey Discussion Draft". Web. Published: Apr. 20, 2009. Accessed: Jul. 1, 2010. Printed: Jun. 13, 2011, <http://www.epa.gov/climatechange/economics/pdfs/WM-Analysis.pdf>.

Notice of Allowance for U.S. Appl. No. 13/027,181 Applicant: McAlister Technologies, LLC; Mailed on Feb. 6, 2012; 11 pages.

First Action Interview Office Action for U.S. Appl. No. 13/027,181; Applicant: McAlister Technologies, LLC; Mailed on Nov. 16, 2011; 15 pages.

First Action Interview Pilot Program Office Action for U.S. Appl. No. 13/026,990; Applicant: McAlister Technologies, LLC; Date of Mailing: Nov. 16, 2011; 15 pages.

First Action Interview Pilot Program Office Action for U.S. Appl. No. 13/027,015; Applicant: McAlister Technologies, LLC; Date of Mailing: Oct. 6, 2011, 4 pages.

First Action Interview Pilot Program Office Action for U.S. Appl. No. 13/027,215; Applicant: McAlister Technologies, LLC; Date of Mailing: Oct. 27, 2011; 3 pages.

International Search Report and Written Opinion for PCT Application No. PCT/US11/024776; Applicant: McAlister Technologies, LLC; Date of Mailing: Oct. 24, 2011, 9 pages.

U.S. Appl. No. 13/685,075, filed Nov. 26, 2012, McAlister.

U.S. Appl. No. 13/684,743, filed Nov. 26, 2012, McAlister.

U.S. Appl. No. 13/832,740, filed Mar. 15, 2013, McAlister.

Solar Collectors, Energy Storage, and Materials, pp. 443-444 (DeWinter, Francis, 1991).

Wikipedia > Aerogel > Carbon—"Carbon aerogels are also extremely 'black' in the infrared spectrum, reflecting only 0.3% of radiation between 250 nm and 14.3 μm, making them efficient for solar energy collectors," 1 page. Accessed in 2011.

Vegners, Raimonds Maris; "Collodial Carbon and Silica : Their Use in Solar Energy" Table of Contents and Introduction of Thesis, University of Sydney, Feb. 1985, 5 pages.

N. Muradov: "Catalysis of Methane decomposition over elemental carbon", Catalysis Communications, No. 3-4, Jul. 1, 2001, pp. 89-94, p. 89, right-hand column, paragraph 2.

Muradov et al: "Catalytic Dissociation of Hydrocarbons: a Route to CO2-free Hydrogen", 15th Annual Symposium on Catalysis in Petroleum Refining & Petrochemicals.

* cited by examiner

REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS

CROSS-REFERENCE TO RELATED APPLICATIONS

The present application claims priority to and the benefit of U.S. Patent Application No. 61/304,403, filed on Feb. 13, 2010 and titled FULL SPECTRUM ENERGY AND RESOURCE INDEPENDENCE, which is incorporated herein by reference in its entirety. To the extent the foregoing application and/or any other materials incorporated herein by reference conflict with the disclosure presented herein, the disclosure herein controls.

TECHNICAL FIELD

The present technology is directed generally to reactor vessels with transmissive surfaces for producing hydrogen-based fuels and structural elements or building blocks, and associated systems and methods. In particular embodiments, reactor systems with transmissive surfaces can be used to produce clean-burning, hydrogen-based fuels from a wide variety of feedstocks, and can produce structural building blocks from carbon or other elements that are released when forming the hydrogen-based fuels.

BACKGROUND

Renewable energy sources such as solar, wind, wave, falling water, and biomass-based sources have tremendous potential as significant energy sources, but currently suffer from a variety of problems that prohibit widespread adoption. For example, using renewable energy sources in the production of electricity is dependent on the availability of the sources, which can be intermittent. Solar energy is limited by the sun's availability (i.e., daytime only), wind energy is limited by the variability of wind, falling water energy is limited by droughts, and biomass energy is limited by seasonal variances, among other things. As a result of these and other factors, much of the energy from renewable sources, captured or not captured, tends to be wasted.

The foregoing inefficiencies associated with capturing and saving energy limit the growth of renewable energy sources into viable energy providers for many regions of the world, because they often lead to high costs of producing energy. Thus, the world continues to rely on oil and other fossil fuels as major energy sources because, at least in part, government subsidies and other programs supporting technology developments associated with fossil fuels make it deceptively convenient and seemingly inexpensive to use such fuels. At the same time, the replacement cost for the expended resources, and the costs of environment degradation, health impacts, and other by-products of fossil fuel use are not included in the purchase price of the energy resulting from these fuels.

In light of the foregoing and other drawbacks currently associated with sustainably producing renewable resources, there remains a need for improving the efficiencies and commercial viabilities of producing products and fuels with such resources.

DETAILED DESCRIPTION

1. Overview

Figure 1:
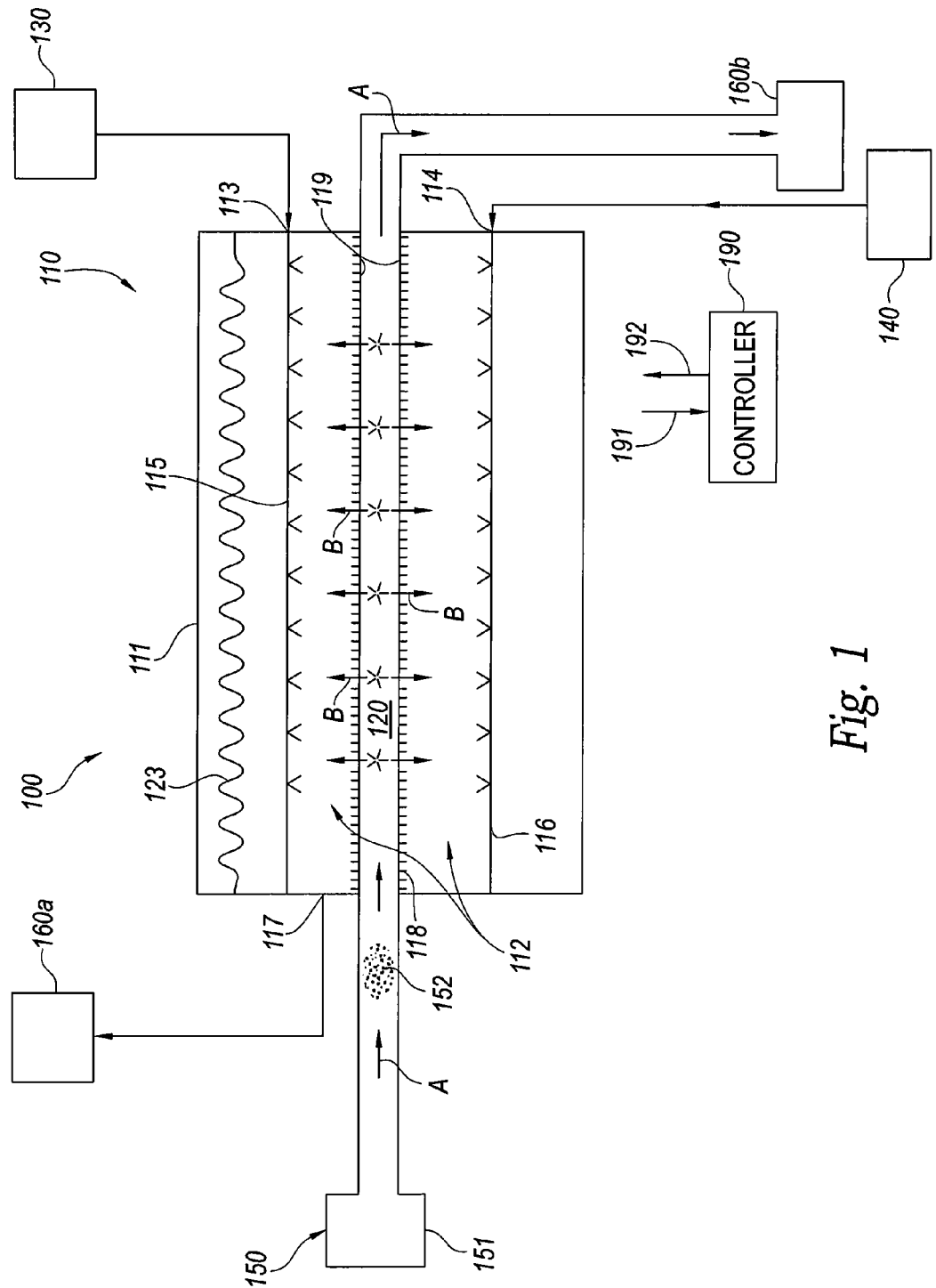
FIG. 1 is a partially schematic, partially cross-sectional illustration of a system having a reactor with transmissive surfaces in accordance with an embodiment of the disclosed technology.

Several examples of devices, systems and methods for producing hydrogen fuels and/or other end products in accordance with the presently disclosed technology are described below. Although the following description provides many specific details of the following examples in a manner sufficient to enable a person skilled in the relevant art to practice, make and use them, several of the details and advantages described below may not be necessary to practice certain examples of the technology. Additionally, the technology may include other examples that are within the scope of the claims but are not described here in detail.

References throughout this specification to "one example," "an example," "one embodiment" or "an embodiment" mean that a particular feature, structure, process or characteristic described in connection with the example is included in at least one example of the present technology. Thus, the occurrences of the phrases "in one example," "in an example," "one embodiment" or "an embodiment" in various places throughout this specification are not necessarily all referring to the same example. Furthermore, the particular features, structures, routines, steps or characteristics may be combined in any suitable manner in one or more examples of the technology. The headings provided herein are for convenience only and are not intended to limit or interpret the scope or meaning of the claimed technology.

Certain embodiments of the technology described below may take the form of computer-executable instructions, including routines executed by a programmable computer or controller. Those skilled in the relevant art will appreciate that the technology can be practiced on computer or controller systems other than those shown and described below. The technology can be embodied in a special-purpose computer, controller, or data processor that is specifically programmed, configured or constructed to perform one or more of the computer-executable instructions described below. Accordingly, the terms "computer" and "controller" as generally used herein refer to any data processor and can include internet appliances, hand-held devices, multi-processor systems, programmable consumer electronics, network computers, mini-computers, and the like. The technology can also be practiced in distributed environments where tasks or modules are performed by remote processing devices that are linked through a communications network. Aspects of the technology described below may be stored or distributed on computer-readable media, including magnetic or optically readable or removable computer discs as well as media distributed electronically over networks. In particular embodiments, data structures and transmissions of data particular to aspects of the technology are also encompassed within the scope of the present technology. The present technology encompasses both methods of programming computer-readable media to perform particular steps, as well as executing the steps.

A chemical reactor in accordance with a particular embodiment includes a reactor vessel having a reaction zone. A hydrogen donor source and a steam source are coupled in fluid communication with the reaction zone of the reactor vessel. The reactor further includes a transmissive surface at the reactor zone, with the transmissive surface being transmissive to a reactant entering the reaction zone, and/or to radiant energy entering the reaction zone. For example, the transmissive surface can allow radiant energy and/or water vapor present in a combustion products waste stream to enter the reaction zone to facilitate a process for dissociating methane into hydrogen and carbon monoxide.

A representative chemical process in accordance with an embodiment of the disclosure includes directing a hydrogen donor and steam into a reaction zone of a reactor vessel. The method can further include directing radiant energy and/or a reactant through a transmissive surface bounding the reaction zone. The method further includes dissociating the hydrogen donor into dissociation products in the reaction zone, and forming a non-hydrogen-based structural building block and a hydrogen-based fuel from the dissociation products. These products are then removed from the reaction zone so that, in particular examples, the fuel can be combusted or provided to a fuel cell, and the building block can be used to produce a polymer or other durable good.

2. Representative Reactors and Associated Methodologies

FIG. 1 is a partially schematic illustration of a system 100 that includes a reactor 110. The reactor 110 further includes a reactor vessel 111 that encloses or partially encloses a reaction zone 112. The reactor vessel 111 has one or more transmissive surfaces positioned to facilitate the chemical reaction taking place within the reaction zone 112. In a representative example, the reactor vessel 111 receives a hydrogen donor provided by a donor source 130 to a donor entry port 113. For example, the hydrogen donor can include a nitrogenous compound such as ammonia or a compound containing carbon and hydrogen such as methane or another hydrocarbon. The hydrogen donor can be suitably filtered before entering the reaction zone 112 to remove contaminants, e.g., sulfur. A donor distributor or manifold 115 within the reactor vessel 111 disperses or distributes the hydrogen donor into the reaction zone 112. The reactor vessel 111 also receives an oxygen donor such as an alcohol or steam from a steam/water source 140 via a steam entry port 114. A steam distributor 116 in the reactor vessel 111 distributes the steam into the reaction zone 112. The reactor vessel 111 can further include a heater 123 that supplies heat to the reaction zone 112 to facilitate endothermic reactions. Such reactions can include dissociating a compound such as a nitrogenous compound, or a compound containing hydrogen and carbon such as methane or another hydrocarbon into hydrogen or a hydrogen compound, and carbon or a carbon compound. The products of the reaction exit the reactor vessel 111 via an exit port 117 and are collected at a reaction product collector 160a.

The system 100 can further include a source 150 of radiant energy and/or additional reactants, which provides constituents to a passage 118 within the reactor vessel 111. For example, the radiant energy/reactant source 150 can include a combustion chamber 151 that provides hot combustion products 152 to the passage 118, as indicated by arrow A. A combustion products collector 160b collects combustion products exiting the reactor vessel 111 for recycling and/or other uses. In a particular embodiment, the combustion products 152 can include carbon dioxide, carbon monoxide, water vapor, and other constituents. One or more transmissive surfaces 119 are positioned between the reaction zone 112 (which can be disposed annularly around the passage 118) and an interior region 120 of the passage 118. The transmissive surface 119 can accordingly allow radiant energy and/or a chemical constituent to pass radially outwardly from the passage 118 into the reaction zone 112, as indicated by arrows B. By delivering the radiant energy and/or chemical constituent(s) provided by the flow of combustion products 152, the system 100 can enhance the reaction taking place in the reaction zone 112, for example, by increasing the reaction zone temperature and/or pressure, and therefore the reaction rate, and/or the thermodynamic efficiency of the reaction. Similarly, a chemical constituent such as water or steam can be recycled or otherwise added from the passage 118 to replace water or steam that is consumed in the reaction zone 112. In a particular aspect of this embodiment, the combustion products and/or other constituents provided by the source 150 can be waste products from another chemical process (e.g., an internal combustion process). Accordingly, the foregoing process can recycle or reuse energy and/or constituents that would otherwise be wasted, in addition to facilitating the reaction at the reaction zone 112.

The composition and structure of the transmissive surface 119 can be selected to allow radiant energy to readily pass from the interior region 120 of the passage 118 to the reaction zone 112. For example, the transmissive surface 119 can include glass or another material that is transparent or at least partially transparent to infrared energy and/or radiant energy at other wavelengths that are useful for facilitating the reaction in the reaction zone 112. In many cases, the radiant energy is present in the combustion product 152 as an inherent result of the combustion process. In other embodiments, an operator can introduce additives into the stream of combustion products 152 to increase the amount of energy extracted from the stream and delivered to the reaction zone 112 in the form of radiant energy. For example, the combustion products 152 can be seeded with sodium, potassium, and/or magnesium, which can absorb energy from the combustion products 152 and radiate the energy outwardly through the transmissive surface 119. In particular embodiments, the walls of the reaction zone 112 can be dark and/or can have other treatments that facilitate drawing radiant energy into the reaction zone 112. However, it is also generally desirable to avoid forming particulates and/or tars, which may be more likely to form on dark surfaces. Accordingly, the temperature on the reaction zone 112 and the level of darkness can be controlled/selected to produce or to prevent tar/particulate formation.

In particular embodiments, the process performed at the reaction zone includes a conditioning process to produce darkened radiation receiver zones, for example, by initially providing heat to particular regions of the reaction zone 112. After these zones have been heated sufficiently to cause dissociation, a small amount of a hydrogen donor containing carbon is introduced to cause carbon deposition or deposition of carbon-rich material. Such operations may be repeated as needed to restore darkened zones as desired.

In another particular aspect of this embodiment, the process can further includes preventing undesirable solids or liquids, such as particles and/or tars produced by dissociation of carbon donors, from forming at certain areas and/or blocking passageways including the entry port 113 and the distributor 115. This can be accomplished by supplying heat from the heater 123 and/or the transmissive surface 119 to an oxygen donor (such as steam) to heat the oxygen donor. When the oxygen donor is heated sufficiently, it can supply the required endothermic heat and react with the carbon donor without allowing particles or tar to be formed. For example, a carbon donor such as methane or another compound containing carbon and hydrogen receives heat from steam to form carbon monoxide and hydrogen and thus avoids forming of undesirable particles and/or tar.

As noted above, the combustion products 152 can include steam and/or other constituents that may serve as reactants in the reaction zone 112. Accordingly, the transmissive surface 119 can be manufactured to selectively allow such constituents into the reaction zone 112, in addition to or in lieu of admitting radiant energy into the reaction zone 112. In a particular embodiment, the transmissive surface 119 can be formed from a carbon crystal structure, for example, a layered graphene structure. The carbon-based crystal structure can include spacings (e.g., between parallel layers oriented transverse to the flow direction A) that are deliberately selected to allow water molecules to pass through. At the same time, the spacings can be selected to prevent useful reaction products produced in the reaction zone 112 from passing out of the reaction zone. Suitable structures and associated methods are further disclosed in pending U.S. patent application Ser. No. 13/027,214 titled, "ARCHITECTURAL CONSTRUCT HAVING FOR EXAMPLE A PLURALITY OF ARCHITECTURAL CRYSTALS" filed concurrently herewith and incorporated herein by reference. The structure used to form the transmissive surface 119 can be carbon-based, as discussed above, and/or can be based on other elements capable of forming a self-organized structures, or constituents capable of modifying the surface of 119 to pass or re-radiate particular radiation frequencies, and/or block or pass selected molecules. Such elements can include transition metals, boron, nitrogen, silicon, and sulfur, among others. In particular embodiments, the transmissive surface 119 can include re-radiating materials selected to re-radiate energy at a wavelength that is particularly likely to be absorbed by one or more reactants in the reaction zone 112. The walls of the reaction zone 112 can include such material treatments in addition to or in lieu of providing such treatments to the transmissive surface 119. Further details of such structures, materials and treatments are disclosed in co-pending U.S. patent application Ser. No. 13/027,015 titled, "CHEMICAL REACTORS WITH RE-RADIATING SURFACES AND ASSOCIATED SYSTEMS AND METHODS" filed concurrently herewith and incorporated herein by reference.

The system 100 can further include a controller 190 that receives input signals 191 (e.g., from sensors) and provides output signals 192 (e.g., control instructions) based at least in part on the inputs 191. Accordingly, the controller 190 can include suitable processor, memory and I/O capabilities. The controller 190 can receive signals corresponding to measured or sensed pressures, temperatures, flow rates, chemical concentrations and/or other suitable parameters, and can issue instructions controlling reactant delivery rates, pressures and temperatures, heater activation, valve settings and/or other suitable actively controllable parameters. An operator can provide additional inputs to modify, adjust and/or override the instructions carried out autonomously by the controller 190.

One feature of forming the transmissive surface 119 from graphene or other crystal structures is that it can allow both radiant energy and useful constituents (e.g., water) to pass into the reaction zone 112. In a particular embodiment, the spacing between graphene layers can be selected to "squeeze" or otherwise orient water molecules in a manner that tends to present the oxygen atom preferentially at the reaction zone 112. Accordingly, those portions of the reaction that use the oxygen (e.g., oxidation or oxygenation steps) can proceed more readily than they otherwise would. As a result, this mechanism can provide a further avenue for facilitating the process of dissociating elements or compounds from the hydrogen donor and water, (and/or other reactants) and reforming suitable end products. Steps for carrying out this process are described further below with reference to FIG. 2.

Figure 2:
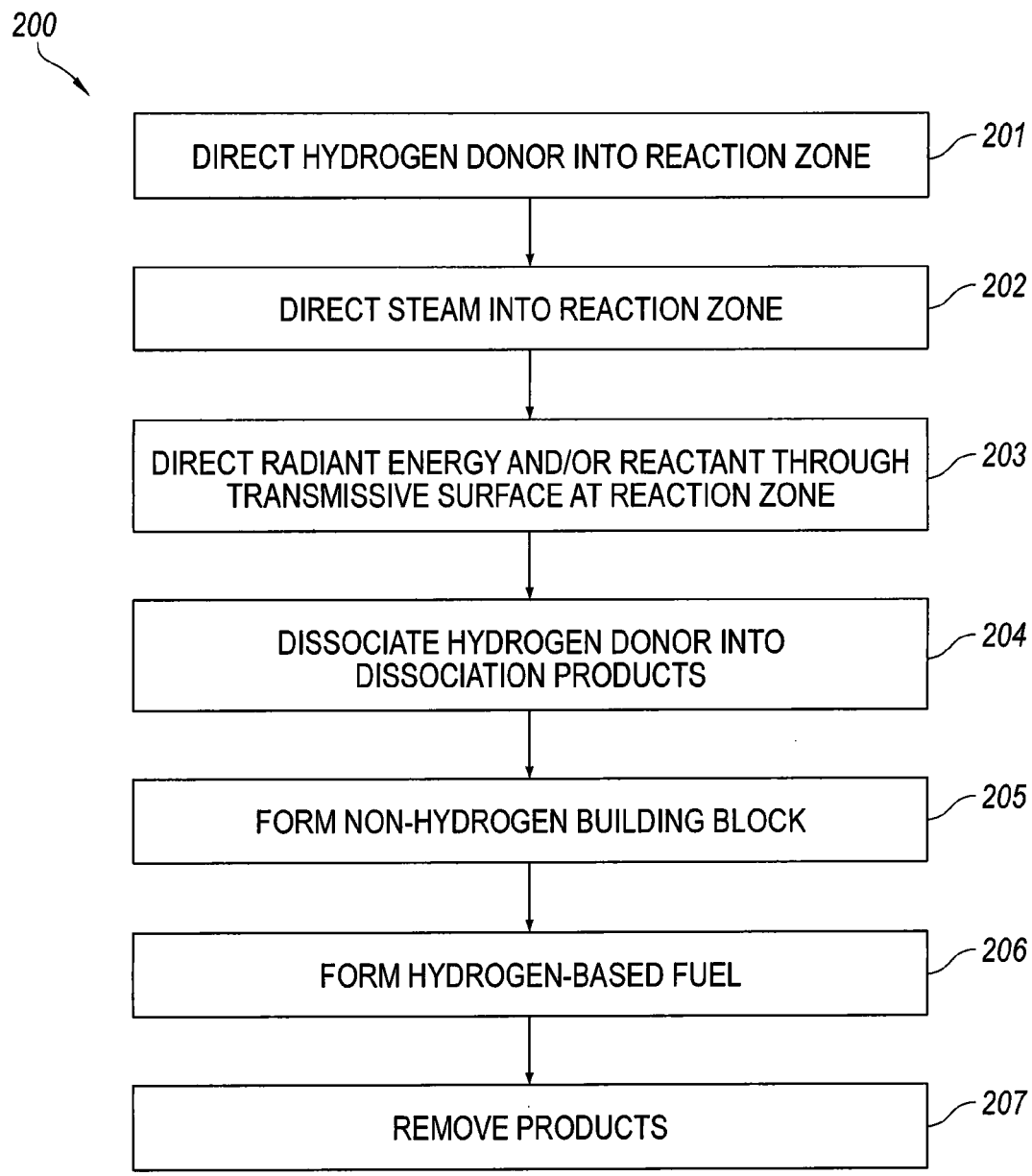
FIG. 2 is a flow diagram illustrating a representative process for producing reaction products with a reactor having a transmissive surface in accordance with an embodiment of the disclosed technology.

FIG. 2 is a flow diagram illustrating representative steps or process portions that are carried out in an overall process 200 for forming useful products from input reactants. The process elements of FIG. 2 can be conducted in accordance various priorities, or in parallel, or in other arrangements including prioritizing steam heating to provide sufficient heat for reactions involving the hydrogen donor without forming particles or tar.

Process portion 201 includes directing a hydrogen donor into a reaction zone. As discussed above, the hydrogen donor can include methane in some embodiments, and other hydrocarbons in other embodiments. Such hydrocarbons can include gasoline, diesel fuel, kerosene, bunker fuel, and/or other suitable organic or organically derived compounds. In other embodiments, the hydrogen donor need not be carbon-based. For example, the hydrogen donor can include ammonia (a nitrogen-based hydrogen donor). In general, the hydrogen donor is selected not only for its ability to deliver hydrogen atoms to the reaction zone, but also for its ability to provide atoms that, after dissociation, can form structural building blocks that are used to form end products other than the hydrogen-based fuel. For example, when the hydrogen donor is carbon-based, the structural building block can include pure carbon, or oxygenated carbon (e.g., carbon monoxide or carbon dioxide) any of which can be used to produce graphene (as discussed above) graphite, or other carbon-based structures that can in turn be processed to form a myriad of commercially useful articles. In particular examples, the carbon building block can be further processed to produce polymers, which can be used to form polymer films and/or other commercially useful polymer-based structures. In still further embodiments, the building blocks can be used to form any of a myriad of other goods, e.g., durable goods.

Representative processes that may be conducted in the reaction zone are identified below:

$$CH_4 + H_2O + HEAT \rightarrow CO + 3H_2 \qquad [\text{Eqn. 1}]$$

$$CO + H_2 \rightarrow CH_3OH + HEAT \qquad [\text{Eqn. 2}]$$

$$2NH_3 + HEAT \rightarrow N_2 + 3H_2 \qquad [\text{Eqn. 3}]$$

Other suitable processes are disclosed in U.S. patent application Ser. Nos. 13/027,208 and 13/027,068, titled "CHEMICAL PROCESSES AND REACTORS FOR EFFICIENTLY PRODUCING HYDROGEN FUELS AND STRUCTURAL MATERIALS, AND ASSOCIATED SYSTEMS AND METHODS" and "CARBON-BASED DURABLE GOODS AND RENEWABLE FUEL FROM BIOMASS WASTE DISSOCIATION" filed concurrently herewith and incorporated herein by reference.

Process portion 202 includes producing steam from water or directing steam into the reaction zone to facilitate dissociation of the hydrogen donor and/or respeciation of the dissociated constituents into a hydrogen-based fuel and a suitable building block. Process portion 203 includes directing radiant energy and/or a reactant through the transmissive surface of the reaction zone. As discussed above, the radiant energy can facilitate the endothermic aspects of the reactions completed in the reaction zone, and the reactants can contribute the molecules necessary for conducting the reaction. Introducing reactants through the transmissive surface can also increase the pressure of the reaction zone, which can in turn facilitate the reaction taking place there.

In process portion 204, the hydrogen donor is dissociated into dissociation products, which can include pure hydrogen or hydrogen compounds, and pure carbon or carbon compounds. When the hydrogen donor does not include carbon (e.g., in the case of ammonia and/or other nitrogenous compounds), process portion 204 can include forming nitrogen or nitrogen compounds. Process portion 205 includes forming non-hydrogen building blocks (e.g., building blocks formed from carbon, nitrogen, boron, sulfur, or silicon) and process portion 206 includes forming a hydrogen-based fuel. For example, when the hydrogen donor includes methane, the non-hydrogen building block can include carbon monoxide, and the hydrogen-based fuel can include diatomic hydrogen. The foregoing reactions can be conducted in the presence of a suitable catalyst, e.g., nickel, platinum, palladium, iridium, osmium and/or silver, and/or alloys of the foregoing elements. In particular embodiments, the temperature in the reactor is controlled to prevent and/or remove catalyst contamination. For example, aspects of the presently disclosed technology include preheating the catalysts and continuing to add heat (e.g., via steam) to prevent and/or remove contamination.

In process portion 207, the reaction products are removed. A suitable process (e.g., an adsorption process) can be used to separate the hydrogen-based fuel from the non-hydrogen building block. The hydrogen-based fuel can then be burned to produce clean power, and the building block can form useful end structures, such as those described above. These two main products of the reaction can be used separately, or in combination. In an example of combined use, the hydrogen is burned to produce the energy used to form the commercially-useful end products from the carbon building blocks.

Figure 3:
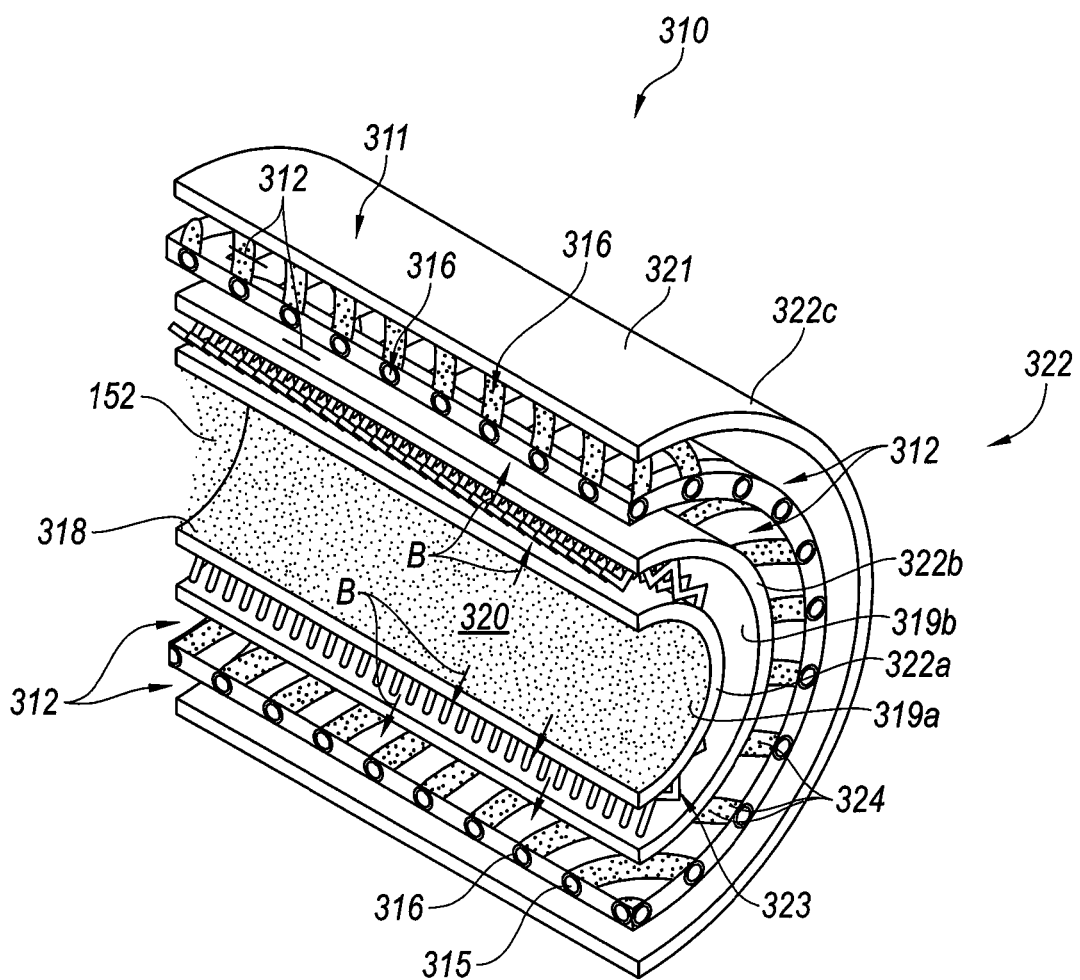
FIG. 3 is a partially schematic, cut-away illustration of a portion of a reactor having transmissive surfaces positioned annularly in accordance with an embodiment of the disclosed technology.

FIG. 3 is a partially schematic, partially cut-away illustration of a reactor 310 that includes a vessel 311 formed from three annularly (e.g., concentrically) positioned conduits 322. Accordingly, the reactor 310 can operate in a continuous flow manner. As used herein, "continuous flow" refers generally to a process in which reactants and products can be provided to and removed from the reactor vessel continuously without halting the reaction to reload the reaction zone with reactants. In other embodiments, the reactor 310 can operate in a batch manner during which reactants are intermittently supplied to the reaction zone and products are intermittently removed from the reaction zone. The three conduits 322 include a first or inner conduit 322a, a second or intermediate conduit 322b, and a third or outer conduit 322c. The first conduit 322a bounds a combustion products passage 318 and accordingly has an interior region 320 through which the combustion products 152 pass. The first conduit 322a has a first transmissive surface 319a through which radiant energy passes in a radially outward direction, as indicated by arrows B. In a particular aspect of this embodiment, the annular region between the first conduit 322a and the second conduit 322b houses a heater 323, and the annular region between the second conduit 322b and the third conduit 322c houses a reaction zone 312. The heater 323 together with the radiant heat from the combustion products 152 provide heat to the reaction zone 312. Accordingly, the second conduit 322b can include a second transmissive surface 319b that allows radiant energy from both the combustion products 152 and the heater 323 to pass radially outwardly into the reaction zone 312. In a particular aspect of this embodiment, the first transmissive surface 319a and the second transmissive surface 319b are not transmissible to chemical constituents of the combustion products 152, in order to avoid contact (e.g., corrosive or other damaging contact) between the combustion products 152 and the heater 323. In another embodiment, the heater 323 can be manufactured (e.g., with appropriate coatings, treatments, or other features) in a manner that protects it from chemical constituents passing through the first and second transmissive surfaces 319a, 319b. In still another embodiment, the heater 323 can be positioned outwardly from the reaction zone 312, as will be described in greater detail below with reference to FIG. 5. In any of these embodiments, the heater 323 can include an electrical resistance heater, an induction heater or another suitable device. In at least some instances, the heater 323 is powered by combusting a portion of the hydrogen produced in the reaction zone 312. in other embodiments, combustion is performed in the reactor itself, for example, with the second conduit 322b serving as a gas mantle for radiating energy at frequencies selected to accelerate the desired reactions in reaction zone 312.

In any of the forgoing embodiments, the reaction zone 312 can house one or more steam distributors 316 and one or more hydrogen donor distributors 315. Each of the distributors 315, 316 can include pores 324 and/or other apertures, openings or passages that allow chemical reactants to enter the reaction zone 312. The donor distributors 315, 316 can include one or more spiral conduits, including, e.g., conduits arranged in a braided fashion to distribute reactants into the reaction zone uniformly in the axial, radial and circumferential directions. The reaction zone 312 is bounded by the third conduit 322c which can have an insulated reactor outer surface 321 to conserve heat within the reaction zone 312. During operation, the reaction taking place in the reaction zone 312 can be controlled by adjusting the rate at which steam and the hydrogen donor enter the reaction zone 312, the rate at which heat enters the reaction zone 312 (via the combustion product passage 318 and/or the heater 323) and other variables, including the pressure at the reaction zone 312. Appropriate sensors and control feedback loops carry out these processes autonomously, with optional controller intervention, as described above with reference to FIG. 1.

Figure 4A:
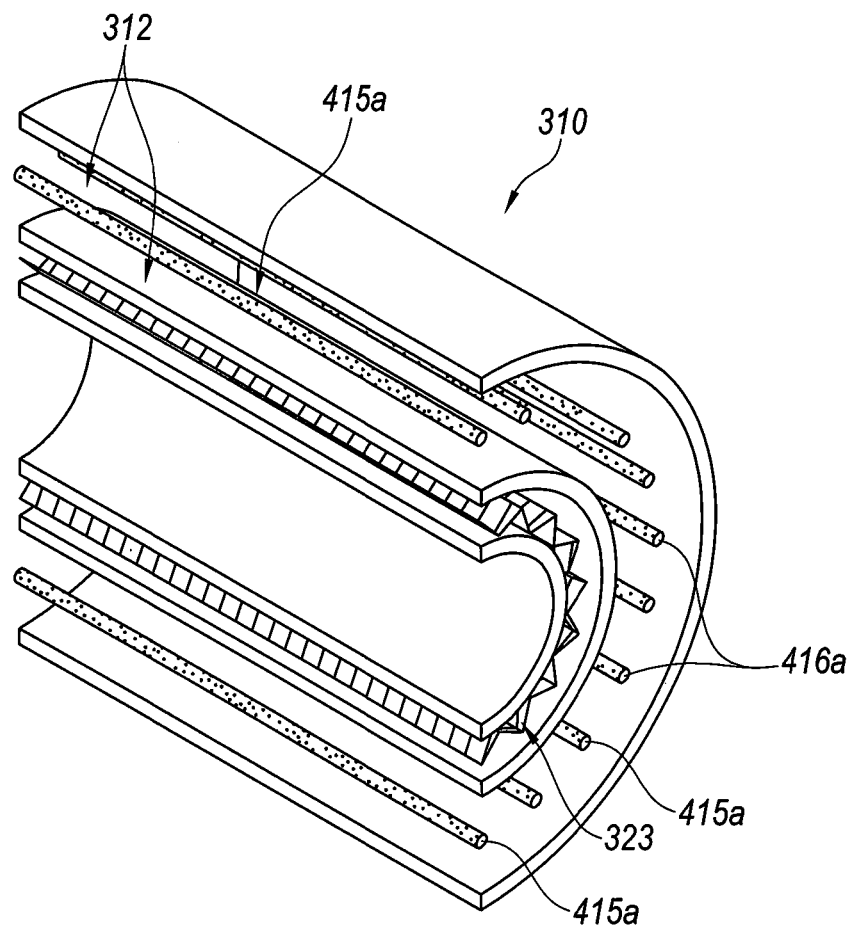
FIG. 4A is a partially schematic, cut-away illustration of a reactor having hydrogen donor distributor manifolds and steam manifolds positioned in accordance with another embodiment of the disclosed technology.
Figure 4B:
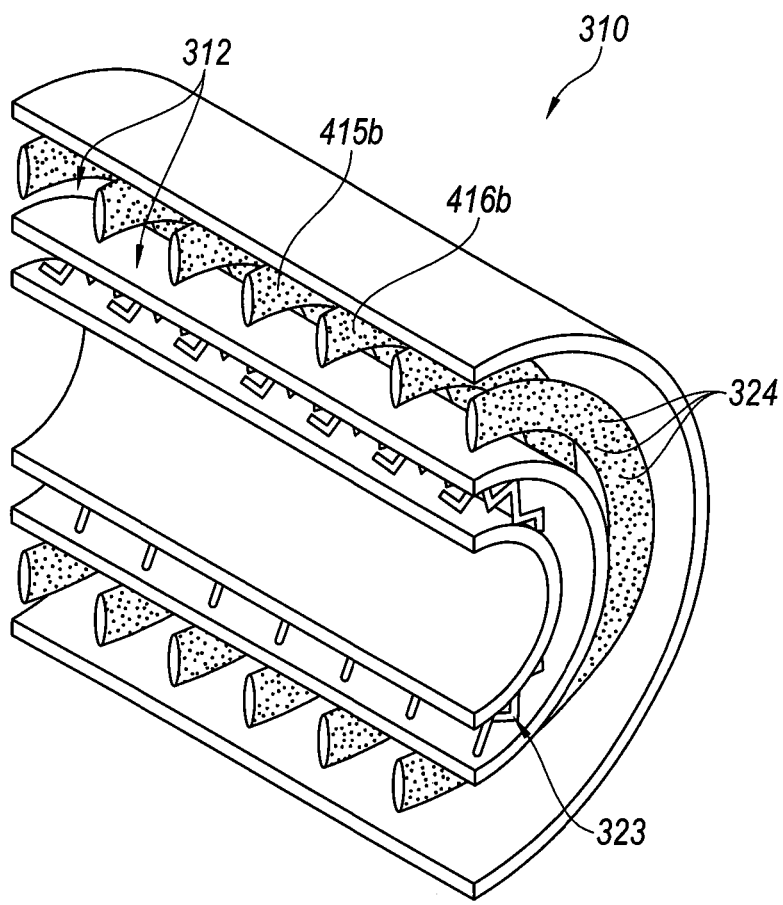
FIG. 4B is a partially schematic, cut-away illustration of a reactor having hydrogen donor distributor manifolds and steam manifolds positioned in accordance with still another embodiment of the disclosed technology.

FIG. 4A is partially schematic, cut-away illustration of portion of the reactor 310 having features generally similar to those described above with reference to FIG. 3, but with a different arrangement of distributors. In particular, the reactor 310 can include a donor distributor 415a that has perforated, axially extending conduits, rather than a spiral conduit. The steam distributor 416a can have a similar geometry. The heater 323 can include radiation mantle features, perforations, slots, spaced-apart coil elements or other features that allow radiant energy and/or constituents to pass radially outwardly into the reaction zone 312. FIG. 4B illustrates another arrangement of the reactor 310 in which a donor distributor 415b and a steam distributor 416b are positioned in a multi-start spiral configuration in the reaction zone 312. The particular arrangement selected for the reactor (e.g., linear, axially extending distributors, or spiral distributors) can be selected based upon factors that include the rate and uniformity with which the reactants are to be delivered to the reaction zone 312.

Figure 5:
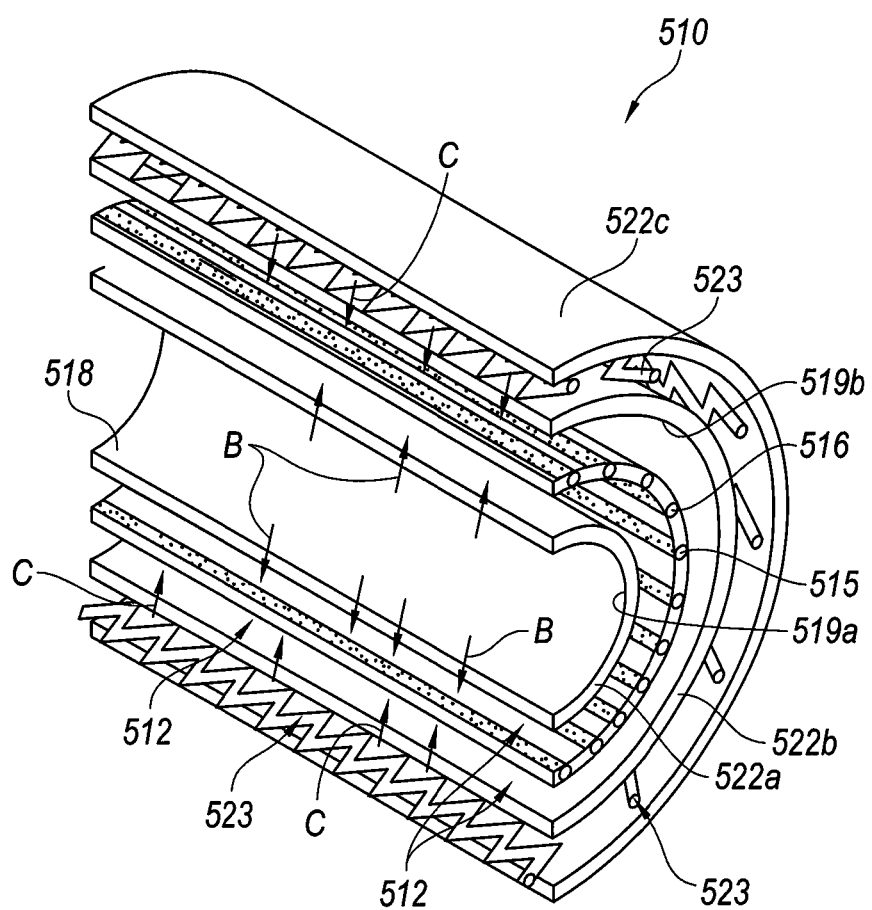
FIG. 5 is partially schematic, cut-away illustration of a reactor having transmissive surfaces oriented annularly in accordance with another embodiment of the disclosure.

FIG. 5 is a partially schematic, cut-away illustration of a reactor 510 having a heater 523 positioned annularly outwardly, rather than inwardly, from a corresponding reaction zone 512, in accordance with another embodiment of the technology. In this embodiment, the reactor 510 includes an inner conduit 522a bounding a combustion products passage 518, a second or intermediate conduit 522b positioned annularly outwardly from the first conduit 522a, and a third or outer conduit 522c positioned annularly outwardly from the second conduit 522b. The reaction zone 512 is positioned between the first and second conduits 522a, 522b, and the heater 523 is positioned between the second and third conduits 522b, 522c. Accordingly, the inner conduit 522a can include a first transmissive surface 519a that is transmissive to radiant energy and/or reactants, as indicated by arrows B. The first transmissive surface 519a need not prevent the passage of reactants to protect the heater 523 (as was discussed above with reference to FIG. 3) because the heater 523 is positioned outwardly from the reaction zone 512. The second conduit 522b can include a second transmissive surface 519b that is transmissive to radiant energy from the heater 523, as indicated by arrows C, but can be non-transmissive to chemical species, to prevent constituents from traveling radially outwardly from the reaction zone 512. The reactor 510 can further include hydrogen donor distributors 515 and steam distributors 516 which can be linear as shown in FIG. 5, or spiral, (e.g., as shown in FIG. 3).

Figure 6:
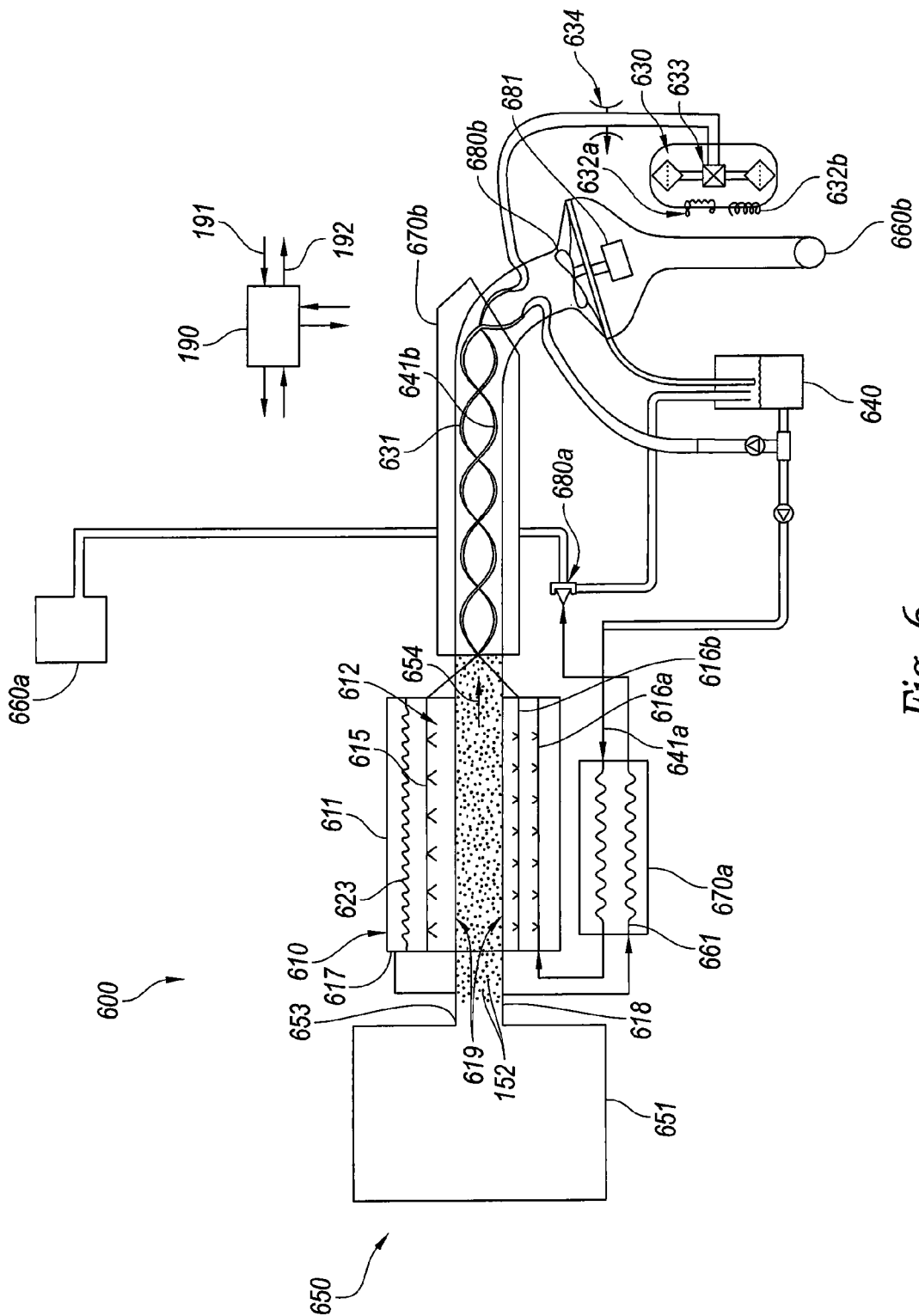
FIG. 6 is a partially schematic illustration of a system that includes a reactor in combination with counter-flow heat exchangers in accordance with an embodiment of the disclosure.

FIG. 6 is a partially schematic illustration of system 600 that includes a reactor 610 in combination with heat exchangers and separators configured to transfer heat and segregate products in accordance with another embodiment of the disclosure. In a particular aspect of this embodiment, the system 600 includes a steam/water source 640 that provides steam to a reactor vessel 611 to facilitate product formation. Steam from the steam/water source 640 can be provided to the reactor 610 via one or more channels. In a particular embodiment, a first channel includes a first water path 641a that passes through a first heat exchanger 670a and into the reactor vessel 611 via a first steam distributor 616a. Products removed from the reactor vessel 611 pass through a reactor product exit port 617 and along a products path 661. The products path 661 passes through the first heat exchanger 670a in a counter-flow or counter-current manner to cool the products and heat the steam entering the reactor vessel 611. The products continue to a reaction product separator 680a that segregates useful end products (e.g., hydrogen and carbon or carbon compounds) which are then collected at products collector 660a. Water remaining in the products path 661 can be separated at the reaction product separator 680a and returned to the steam/water source 640.

A second channel via which the steam/water source 640 provides steam to the reactor 610 includes a second water path 641b that passes through a second heat exchanger 670b. Water proceeding along the second water path 641b enters the reactor 610 in the form of steam via a second stream distributor 616b. This water is heated by combustion products that have exited a radiant energy/reactant source 650 (e.g., exited a combustion chamber 651 at a combustion products outlet 653), and passed through the combustion product passage 618 (which includes a transmissive surface 619) along a combustion products path 654. The spent combustion products are collected at a combustion products collector 660b and can include nitrogen compounds, phosphates, used illuminant additives (e.g., compounds including sodium, magnesium and/or potassium), and/or other compositions that may be recycled or used for other purposes (e.g., agricultural purposes.)

In addition to heating water along the second water path 641b and cooling the combustion products along the combustion products path 654, the second heat exchanger 670b can heat the hydrogen donor passing along a donor path 631 to a donor distributor 615 located within the reactor vessel 611. In particular, the system 600 can include a donor vessel 630 that houses a hydrogen donor, e.g., a hydrocarbon such as gasoline, biodiesel fuel, propane, methane, fuel alcohols, and/or hydrogen, or a nitrogenous donor such as ammonia. The donor vessel 630 can include one or more heaters 632 (shown as first heater 632a and a second heater 632b) to vaporize and/or pressurize the hydrogen donor within. A three-way valve 633 and regulator 634 control the amount of fluid and/or vapor that exits the donor vessel 630 and passes along the donor path 631 through the heat exchanger 670b and into the reactor vessel 611. This enables cold starting with a gaseous fuel such as hydrogen that is delivered through the valve 633 from the top of the donor vessel 630, and subsequent operation on a liquid fuel such as biodiesel or vegetable oil that is subsequently delivered through the valve 633.

In the reactor vessel 611, the combustion products 152 pass through the combustion products passage 618 while delivering radiant energy and/or reactants through the transmissive surface 619 into the reaction zone 612. After passing through the second heat exchanger 670b, the combustion products 152 can enter a combustion products separator 680b that separates water from the combustion products. Separated water returns to the steam/water source 640 and the remaining combustion products are collected at the combustion products collector 660b. In a particular embodiment, the separator 680b can include a centrifugal separator that is driven by the kinetic energy of the combustion product stream. If the kinetic energy of the combustion product stream is insufficient to separate the water by centrifugal force, a motor/generator 681 can add energy to the separator 680b to provide the necessary centrifugal force. If the kinetic energy of the combustion product stream is greater than is necessary to separate water, the motor/generator 681 can produce energy, e.g., to be used by other components of the system 600. The controller 190 receives inputs from the various elements of the system 600 and controls flow rates, pressures, temperatures, and/or other parameters.

One feature of at least some of the foregoing embodiments described above is that the reactors can include transmissive surfaces that allow radiant energy and/or chemical constituents to pass into the reaction zone from a region outside the reaction zone. An advantage of this feature is that it can facilitate the chemical process taking place within the reaction zone, while making use of available radiant energy and/or constituents that may be present as part of another reaction. For example, this arrangement can be used to extract beneficial thermal and chemical energy from a waste heat stream such as that produced by a combustion process. The reaction itself can result in clean-burning hydrogen and a re-purposed carbon building block.

Another feature of at least some of the foregoing embodiments is that the reactor system can include internal heat exchangers that reduce internal losses by recycling heat. For example, such heat exchangers can be used to cool the combustion products and/or chemical reaction products, while heating incoming steam and/or other incoming chemical reactants.

Still another advantage of at least some of the foregoing embodiments is that the transmissive surface can include a crystal structure, for example, a carbon-based graphene that is not only selective to radiant energy and chemical reactants, but can pass the chemical reactants (e.g., water) into the reaction zone in a manner that further facilitates the reaction therein. The foregoing features, alone or in combination can improve the overall efficacy, efficiency, and commercial viability of the reactor systems.

From the forgoing, it will appreciated that specific embodiments of the technology have been described herein for purposes of illustration, but that various modifications may be made without deviating from the technology. For example, the radiant energy/reactant source 150 can deliver a fluid other than a combustion products stream to the transmissive surface. Examples described above in the context of carbon-based reactants can be performed in generally similar manners or other reactants including boron, nitrogen, silicon, or sulfur-based reactants.

Certain aspects of the technology described in the context of particular embodiments may be combined or eliminated in other embodiments. For example, any of the reactors described above in the context of FIG. 3-5 can be used in the systems of FIGS. 1 and 6. In particular embodiments, the steam distributors can be eliminated if sufficient steam is available via the transmissive surface to conduct the reaction and, if necessary, cools the reaction. Further while advantages associated with certain embodiments of the technology have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

To the extent not previously incorporated herein by reference, the present application incorporates by reference in their entirety the subject matter of each of the following materials: U.S. patent application Ser. No. 12/857,553, filed on Aug. 16, 2010 and titled SUSTAINABLE ECONOMIC DEVELOPMENT THROUGH INTEGRATED PRODUCTION OF RENEWABLE ENERGY, MATERIALS RESOURCES, AND NUTRIENT REGIMES; U.S. patent application Ser. No. 12/857,553, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE ENERGY; U.S. patent application Ser. No. 12/857,554, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE MATERIAL RESOURCES USING SOLAR THERMAL; U.S. patent application Ser. No. 12/857,502, filed on Aug. 16, 2010 and titled ENERGY SYSTEM FOR DWELLING SUPPORT; U.S. patent application Ser. No. 13/027,235, filed on Feb. 14, 2011 and titled DELIVERY SYSTEMS WITH IN-LINE SELECTIVE EXTRACTION DEVICES AND ASSOCIATED METHODS OF OPERATION; U.S. Patent Application No. 61/401,699, filed on Aug. 16, 2010 and titled COMPREHENSIVE COST MODELING OF AUTOGENOUS SYSTEMS AND PROCESSES FOR THE PRODUCTION OF ENERGY, MATERIAL RESOURCES AND NUTRIENT REGIMES; U.S. patent application Ser. No. 13/027,208, filed on Feb. 14, 2011 and titled CHEMICAL PROCESSES AND REACTORS FOR EFFICIENTLY PRODUCING HYDROGEN FUELS AND STRUCTURAL MATERIALS, AND ASSOCIATED SYSTEMS AND METHODS; U.S. patent application Ser. No. 13/027,015, filed on Feb. 14, 2011 and titled CHEMICAL REACTORS WITH RE-RADIATING SURFACES AND ASSOCIATED SYSTEMS AND METHODS; U.S. patent application Ser. No. 13/027,244, filed on Feb. 14, 2011 and titled THERMAL TRANSFER DEVICE AND ASSOCIATED SYSTEMS AND METHODS; U.S. patent application Ser. No. 13/026,990, filed on Feb. 14, 2011 and titled CHEMICAL REACTORS WITH ANNULARLY POSITIONED DELIVERY AND REMOVAL DEVICES, AND ASSOCIATED SYSTEMS AND METHODS; U.S. patent application Ser. No. 13/027,181, filed on Feb. 14, 2011 and titled REACTORS FOR CONDUCTING THERMOCHEMICAL PROCESSES WITH SOLAR HEAT INPUT, AND ASSOCIATED SYSTEMS AND METHODS; U.S. patent application Ser. No. 13/027,215, filed on Feb. 14, 2011 and titled INDUCTION FOR THERMOCHEMICAL PROCESS, AND ASSOCIATED SYSTEMS AND METHODS; U.S. patent application Ser. No. 13/027,198, filed on Feb. 14, 2011 and titled COUPLED THERMOCHEMICAL REACTORS AND ENGINES, AND ASSOCIATED SYSTEMS AND METHODS; U.S. Patent Application No. 61/385,508, filed on Sep. 22, 2010 and titled REDUCING AND HARVESTING DRAG ENERGY ON MOBILE ENGINES USING THERMAL CHEMICAL REGENERATION; U.S. patent application Ser. No. 13/027,060, filed on Feb. 14, 2011 and titled REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS; U.S. patent Ser. No. 13/027,214, filed on Feb. 14, 2011 and titled ARCHITECTURAL CONSTRUCT HAVING FOR EXAMPLE A PLURALITY OF ARCHITECTURAL CRYSTALS; U.S. patent application Ser. No. 12/806,634, filed on Aug. 16, 2010 and titled METHODS AND APPARATUSES FOR DETECTION OF PROPERTIES OF FLUID CONVEYANCE SYSTEMS; U.S. patent application Ser. No. 13/027,188, filed on Feb. 14, 2011 and titled METHODS, DEVICES, AND SYSTEMS FOR DETECTING PROPERTIES OF TARGET SAMPLES; U.S. patent application Ser. No. 13/027,068, filed on Feb. 14, 2011 and titled SYSTEM FOR PROCESSING BIOMASS INTO HYDROCARBONS, ALCOHOL VAPORS, HYDROGEN, CARBON, ETC.; U.S. patent application Ser. No. 13/027,196, filed on Feb. 14, 2011 and titled CARBON RECYCLING AND REINVESTMENT USING THERMOCHEMICAL REGENERATION; U.S. patent application Ser. No. 13/027,195, filed on Feb. 14, 2011 and titled OXYGENATED FUEL; U.S. Patent Application No. 61/237,419, filed on Aug. 27, 2009 and titled CARBON SEQUESTRATION; U.S. Patent Application No. 61/237,425, filed on Aug. 27, 2009 and titled OXYGENATED FUEL PRODUCTION; U.S. patent application Ser. No. 13/027,197, filed on Feb. 14, 2011 and titled MULTI-PURPOSE RENEWABLE FUEL FOR ISOLATING CONTAMINANTS AND STORING ENERGY; U.S. Patent Application No. 61/421,189, filed on Dec. 8, 2010 and titled LIQUID FUELS FROM HYDROGEN, OXIDES OF CARBON, AND/OR NITROGEN; AND PRODUCTION OF CARBON FOR MANUFACTURING DURABLE GOODS; and U.S. patent Ser. No. 13/027,185, filed on Feb. 14, 2011 and titled ENGINEERED FUEL STORAGE, RESPECIATION AND TRANSPORT.

I claim:
1. A chemical reactor, comprising:
a reactor vessel having a reaction zone, the reaction zone coupled in fluid communication with a hydrogen donor source;

a heater positioned annularly outward from the reaction zone of the reactor vessel, the heater producing a first radiant energy;

a transmissive layer positioned between the heater and the reaction zone, the transmissive layer capable of allowing the first radiant energy to pass from the heater to the reaction zone;

a combustion products passage positioned annularly inward from the reaction zone to allow the passage of i) a plurality of reactants and (ii) a second radiant energy from a combustion chamber, one end of the combustion products passage being in fluid communication with the combustion chamber; and another transmissive layer positioned between the combustion products passage and the reaction zone, the another transmissive layer capable of both (a) allowing at least one of the plurality of reactants to pass from the combustion products passage into the reaction zone and (b) restricting at least another one of the plurality of reactants from passing from the combustion products passage into the reaction zone.

2. The reactor of claim 1 wherein the transmissive layer includes a composite of permeable, single-atom layers of carbon, nitrogen or boron.

3. The reactor of claim 1 wherein the reactor vessel is a flow-through vessel having at least one inlet port positioned to receive a second plurality of reactants and at least one outlet port positioned to deliver products.

4. The reactor of claim 3, further comprising a separator coupled to the at least one outlet port of the reactor to receive reaction products from the reactor and separate condensed water from other reaction products.

5. The reactor of claim 1 wherein the another transmissive layer includes a carbon crystal structure that is capable of allowing both infrared radiation and water vapor to pass from the combustion products passage into the reaction zone.

6. The reactor of claim 1 wherein the hydrogen donor source includes a source of a hydrocarbon.

7. The reactor of claim 1 wherein the hydrogen donor source includes a source of a hydrogen and nitrogen.

8. The reactor of claim 1 wherein the another transmissive layer is capable of allowing infrared radiation to pass from the combustion products passage into the reaction zone.

9. The reactor of claim 1 wherein the another transmissive layer is capable of allowing visible radiation to pass from the combustion products passage into the reaction zone.

10. The reactor of claim 1 wherein the another transmissive layer is capable of allowing water vapor to pass from the combustion products passage into the reaction zone.

11. The reactor of claim 1 wherein the heater includes an electric resistance heater.

12. The reactor of claim 1 wherein the heater includes an induction heater.

13. The reactor of claim 1 wherein the another transmissive layer is positioned adjacent a hot fluid flow path.

14. The reactor of claim 1 wherein the another transmissive layer is capable of allowing radiation emitted from at least one of sodium, potassium and magnesium to pass from the combustion products passage into the reaction zone.

15. The chemical reactor of claim 1,
wherein the reactor vessel includes:
a first steam entry port;
the second steam entry port, with the steam source including at least one water source coupled to the first and second steam entry ports; and
a hydrocarbon entry port coupled to the hydrogen donor source, and wherein the reactor further comprises:

a first heat exchanger coupled between the reactor vessel and the at least one water source, the first heat exchanger having a first flow path for reaction products exiting the reaction zone, and a second flow path for water entering the first steam entry port, the first and second flow paths having a counterflow arrangement;

a separator coupled to the first flow path and positioned to separate condensed steam from a stream of hydrogen and carbon reaction products exiting the reactor vessel; and a second heat exchanger coupled between the reactor vessel, the at least one water source and the hydrocarbon source, the second heat exchanger having a third flow path for combustion products passing through the combustion products passage, a fourth flow path for water entering the second steam entry port, and a fifth flow path for hydrocarbons entering the hydrocarbon entry port, the third flow path having a counterflow arrangement with the fourth and fifth flow paths.

16. The reactor of claim 1, wherein the transmissive layer is capable of only allowing the first radiant energy to pass from the heater to the reaction zone.

17. The reactor of claim 1, wherein the first radiant energy is different from the second radiant energy.

18. The reactor of claim 1, wherein the first radiant energy is the same as the second radiant energy.

19. A chemical reactor, comprising:
a heater that produces radiant energy;
a combustion products passage that allows the passage of a plurality of reactants from a combustion chamber, one end of the combustion products passage being in fluid communication with the combustion chamber; and
a reactor vessel including a reaction zone, the reaction zone being positioned between the heater and the combustion products passage;
a transmissive layer positioned between the heater and the reaction zone, the transmissive layer capable of allowing radiant energy to pass from the heater to the reaction zone; and
another transmissive layer positioned between the combustion products passage and the reaction zone, the another transmissive layer capable of both (a) allowing at least one of the plurality of reactants to pass from the combustion products passage into the reaction zone and (b) restricting at least another one of the plurality of reactants from passing from the combustion products passage into the reaction zone.

20. The reactor of claim 19, wherein the reaction zone is further coupled in fluid communication with a hydrogen donor source.

21. A chemical reactor, comprising:
a heater that produces radiant energy;
a combustion products passage that allows the passage of a plurality of reactants from a combustion chamber;
a reactor vessel including a reaction zone, the reaction zone being positioned between the heater and the combustion products passage;
a first transmissive layer positioned between the heater and the reaction zone, the first transmissive layer capable of allowing radiant energy to pass from the heater to the reaction zone; and
a second transmissive layer positioned between the combustion products passage and the reaction, the second transmissive layer capable of both (a) allowing at least one of the plurality of reactants to pass from the combustion products passage into the reaction zone and (b) restricting at least another one of the plurality of reactants from passing from the combustion products passage into the reaction zone.

22. The reactor of claim 21, further comprising:
a combustion chamber.

23. The reactor of claim 21, wherein the reaction zone is further coupled in fluid communication with a hydrogen donor source.

* * * * *